United States Patent [19]

Shaw, Jr.

[11] 4,233,968
[45] Nov. 18, 1980

[54] IUD ARRANGEMENT

[76] Inventor: Seth T. Shaw, Jr., 30036 Via Borica, Rancho Palos Verdes, Calif. 90274

[21] Appl. No.: 928,093

[22] Filed: Jul. 26, 1978

[51] Int. Cl.$^3$ .............................................. A61F 5/46
[52] U.S. Cl. .................................... 128/130; 424/320
[58] Field of Search ........ 128/127, 129, 130, 260–261, 128/268; 424/16, 19, 294, 320, 324, 326

[56] References Cited

U.S. PATENT DOCUMENTS

| 3,361,790 | 1/1968 | Allen et al. | 424/320 |
| 3,683,006 | 8/1972 | Fried | 424/320 |
| 3,918,443 | 11/1975 | Vennard et al. | 128/260 |
| 3,933,152 | 1/1976 | Moulding | 128/130 |
| 3,967,618 | 7/1976 | Zaffaroni | 128/260 |
| 4,034,749 | 7/1977 | Von Kesserü et al. | 128/260 |
| 4,111,196 | 9/1978 | Emmett | 128/260 |
| 4,111,201 | 9/1978 | Theeuwes | 128/260 |

OTHER PUBLICATIONS

*Nature*, 228:1097, 1970, Shaw et al.
*J. Reprod. Med.*, 5:154, 1970, Westrom et al.
*Brit. Med. J.*, 4:17–19, 1975, Kasonde et al.
Medical Primatology, 1972, Proc. 3rd Conf. exp., Med. Surg. Primates, Lyon 1972, part 1, pp. 317–324, Shaw et al.
*Fert. Steril.*, 25(4):358, 1974, Shaw et al.
*J. Med. Prim*, 2:353, 1973, Poon et al.
*Thromb. Diath. Haemorrh.*, 23(3):486–499, 1970, Geratz.
*Thromb. Diath. Haemorrh.*, 25:391, 1971, Geratz.
*Contraception*, 11:395, 1975, Shaw et al.
*European J. Biochem.*, 6, (1968), 502–506, Markwardt et al.
*Arch. Int.* Pharmacodyn, 194, 359–370, (1971), Geratz et al.
*Experientia*, 25/12, 1969, Geratz.
*Brit. Med. J.*, Oct. 4, 1975, Kasonde et al.
Landmann, H., "Synthetische Hemmstoffe des Plasmins," Fibrinolyse, Budapest, 1969, pp. 169–174.
*J. Med. Chem.*, vol. 16, No. 10, 1973, Coats.
*Thromb. Diath. Haemorrh*, 29:154, 1973, Geratz (Stuttg.).
*Thromb. Diath. Haemorrh*, 33:230, 1975, Geratz et al., (Stuttg.).

*Primary Examiner*—C. Fred Rosenbaum
*Attorney, Agent, or Firm*—Don B. Finkelstein

[57] ABSTRACT

An intrauterine device of the type having an external surface contacting the walls of the uterus after insertion therein, and said device having first walls defining a fluid receiving cavity in at least a portion thereof. A concentrated fluid solution of a drug is present in the cavity and the drug is of the type providing an antifertility and antiproteolytic effect and is selected from the group consisting of aromatic monoamidines, aromatic diamidines and non-aromatic diamidines.

32 Claims, 5 Drawing Figures

IUD ARRANGEMENT

REFERENCE TO RELATED APPLICATIONS

This application is related to my co-filed and co-pending patent applications, Ser. Nos. 927,765 and 928,106.

BACKGROUND OF THE INVENTION

1. Field of the Invention

This invention relates to an improved intrauterine device wherein there is a cavity provided in at least a portion of the intrauterine device and a concentrated fluid solution of a drug providing antifibrinolytic, antifertility and antiproteolytic effect is provided within the cavity. The cavity walls are defined by a polymer having a predetermined permeability for the drug.

2. Description of the Prior Art

Many forms and configurations of intrauterine devices designed to prevent conception in the female have heretofore been utilized. Such devices have been provided in a variety of shapes, such as the "T" device shown in U.S. Pat. No. 3,533,406, the Loop, such as shown in U.S. Pat. No. 3,200,815, a "Y" configuration, generally termed a "Ypsilon" configuration, a ring or modified ring such as the Ota ring, and many modifications thereto, including flat, leaf-like members between various segments of the intrauterine device. Such intrauterine devices which were not provided with any medications associated therewith depended upon their presence in the uterus to prevent conception.

Further, other intrauterine devices (IUDs) have incorporated a controlled release rate medication or drug therein to further aid the anticonceptive action thereof. Such medicated IUDs have generally employed copper or progesterone as the contraceptive or antifertility agent. However, it has been found that copper-releasing intrauterine devices, as well as non-medicated intrauterine devices still resulted in pain and cramping to the wearer, as well as metrorrhagia and menorrhagia. Consequently, the excessive uterine hemorrage, with or without pain, continues to be a leading cause for this type of intrauterine device removal. The progesterone-releasing intrauterine devices are associated with significantly less bleeding than other devices but they appear to be associated with a serious complication apparently produced by the release of progesterone. This complication is ectopic pregnancy.

Nevertheless, the general convenience and safety of intrauterine devices continues to give hope that the IUD may one day provide an ideal method for worldwide population control, since it has been found, statistically, that intrauterine devices can provide effective contraception in a 98-99% range of effectivity, they do not require conscious effort, are less subject to human failings than any other type of contraceptive, their antifertility effect is completely reversible, they have minimal, if any systemic effect, and their effect is confined essentially to the uterus. However, it is believed that even greater antifertility effect can be achieved by utilizing other anticonception agents with an IUD, which agents do not have the serious detrimental side effects noted above.

Consequently, there has been a need for improved medicated intrauterine devices providing greater antifertility effect and in which the side effects of pain, metrorrhagia and/or menorrhagia are reduced or eliminated, and which are not associated with other serious side effects such as ectopic pregnancy.

While the inflammatory response of the endometrium to intrauterine devices has heretofore been known, I have discovered that the chronic response of the endometrium to long-term intrauterine device exposure is more a humoral type of reaction (accompanied by increased vascular permeability with edema and interstitial hemorrhage) than the immunologic or cellular type of response (accompanied by infiltration of immune complexes or of leukocytes, such as plasma cells or neutrophils). However, I have found that there are defects in small endometrial vessels which suggest damage caused by mechanical distortion of the uterine tissues. The defects generally lack hemostatic plugs of platelets and/or fibrin. Further, there is evidence that fibrinolysis is activated in the uterus in response to the presence of an intrauterine device. This activation could result in blockage of normal hemostatic reaction at several levels in the coagulation system. Further, it may initiate, aid, or aggravate humoral inflammation by any one or all of the following mechanisms:

1. Activation of the complement system and histamine release;
2. Activation of prekallikrein; and
3. Release of fibrin degradation fragments.

Histamine can cause vascular dilation and increase vascular permeability. Kallikrein (activated prekallikrein) releases bradykinin which can have an effect similar to histamine and may also cause cramping and pain. Fibrin degradation fragments may enhance the vascular effects of histamine and bradykinin. Combined with distortion of the endometrium caused by myometrial contractility around the relatively inelastic or unyielding IUD, which may also be associated with increased prostaglandin synthesis and release, it may be predicted that excessive bleeding from leaky or broken vessels will occur. For these reasons, incorporation into medicated IUD devices of potent inhibitors of plasminogen activation and plasmin activity (fibrinolytic activity) for the purposes of intrauterine release over an extended time period can provide an alleviation of the aforesaid undesired effects.

It has also heretofore been found that IUD associated uterine hemmorhage can be alleviated by the systemic (oral) intake of the fibrinolytic inhibitors epsilon aminocaproic acid (EACA) and tranexamic acid. I have also demonstrated that an EACA loaded IUD inserted into the uterus of rhesus monkeys provides an ameliorative effect on menstral blood loss, and there was no apparent systemic effect by such medicated devices on fibrinolytic activity in these animals. However, neither EACA nor tranexamic acid would appear to be satisfactory agents for long-time intrauterine medication. First, they are not highly potent anti-fibrinolytic agents and would have to be delivered at a rather high rate into the uterine cavity. Thus, a drug loaded IUD would become exhausted of its medication in a short period of time, or would require an unacceptably large size of device. In addition, EACA and tranexamic acid are small molecules which are highly diffusible and water soluble. Therefore, intrauterine release thereof from a medicated intrauterine device at a steady, constant rate is difficult to control and effective concentrations inside the uterus difficult to maintain. Consequently, inhibitor concentrations of either EACA and tranexamic acid of between $1 \times 10^{-3}$ and $1 \times 10^{-4}$ Mol/liter, which is the concentration of these drugs required to be effective, respectively, over a prolonged period of time is generally not achievable considering the amount of medication which is feasible to load into an IUD and considering the diffusion and solubility properties of these compounds and the rate of water turnover inside the uterus.

While there heretofore has been some indication that certain compounds used for treatment of protozoal, bacterial and fungal infections may have anti-fibrinolytic properties, there has not heretofore been any indication of anti-fertility action of these compounds added to an intrauterine device. These compounds may be generally defined as the aromatic amidines, and in particular, the aromatic diamidines. However, heretofore, it has not been specifically recognized that their anit-fibrinolytic action inside the uterus can alleviate the metrorrhagia and menorrhagia. Further, even though such metrorrhagia and menorrhagia may be alleviated, the pain and cramps associated with intrauterine devices could still remain a major drawback to effective extensive use of medicated intrauterine devices as a population control technique.

In addition to the above-mentioned types of intrauterine devices, there is also heretofore been provided intrauterine devices in which all or a part of the device is hollow and thus the device has walls defining the cavity. Such a device is shown, for example, in U.S. Pat. No. 3,896,819 and other types of such devices are shown, for example, in U.S. Pat. No. 3,710,795 in which the cavity is filled with a solid matrix, and other prior art patents. Similarly, there have heretofore been proposed inflatable intrauterine devices in which the walls of the intrauterine device are flexible and it is inserted into the uterus in uninflated condition and subsequently expanded.

However, in none of the prior art devices has there heretofore been provided a drug releasable at a controlled rate over an extended period of time which drug provides not only an antiproteolytic action but an enhanced contraceptive action. Accordingly, there has long been a need for an intrauterine device which can provide the above desiderata.

Additionally, in many prior art IUDs, expulsion thereof is a somewhat frequent occurrence. Such undesired expulsion is another drawback of prior art IUDs.

Consequently, there has long been a need for a medicated intrauterine device which not only enhances the anti-fertility action of the IUD but also provides reduction or elimination of metrorrhagia or menorrhagia for an extended period of time, as well as decreasing the pain and cramps associated with wearing an intrauterine device, as well as decreasing the tendency of expulsion thereof.

SUMMARY OF THE INVENTION

Accordingly, it is an object of the present invention to provide an improved intra-uterine device.

It is another object of the present invention to provide an improved medicated intra-uterine device of the type enhancing the anti-fertility action of the intra-uterine device.

It is yet another object of the present invention to provide an improved medicated intra-uterine device which reduces metrorrhagia and menorrhagia.

It is yet another object of the present invention to provide an improved intra-uterine device that reduces pain and cramps associated with the utilization of an intra-uterine device, as well as minimizing the explusion thereof.

The anti-proteolytic action and, in particular, the anti-fibrinolytic action of the aromatic monoamidines, aromatic diamidines and non-aromatic diamidines can provide a reduction in metrorrhagia and menorrhagia because of the particular characteristics associated with the reaction of the endometrium and/or the fluid of the uterus to the presence of an intrauterine device. Further, it is believed that inhibition of other proteolytic systems in the endometrium and/or muscle wall of the uterus can reduce and/or eliminate the pain and cramps associated with wearing an intrauterine device, as well as minimizing the risk of expulsion thereof. The amidines and, in particular, the aromatic monoamidines, aromatic diamidines, and non-aromatic diamidines, have been found to possess the desired properties, due to the anti-fibrinolytic and other antiproteolytic effect thereof, to reduce or eliminate metrorrhagia and/or menorrhagia.

Additionally, I have discovered that there is a surprising and unexpected result in utilization of aromatic diamidines with intrauterine devices in that they enhance the anti-fertility effect of the IUD. That is, the may cause a greater contraceptive effect than has heretofore been obtainable with prior art IUDs of either the plain or medicated type. This unexpected result, it is believed, is achieved by the mechanism of the aromatic diamidine acting upon the fertilized egg or the blastocyst (preimplantation embryo) to cause it to degenerate. The aromatic diamidine could, in addition, act on the sperm to either kill or render them ineffective in fertilization.

Further, it is believed, that certain anti-proleolytic action of the aromatic diamidines could reduce or eliminate the pain and cramps often associated with wearing an IUD.

In the present invention, the IUD is in the form of a uterus insertable body member having first walls defining a cavity therein. The cavity may extend throughout the IUD or only for a portion thereof. Further, the walls defining the cavity may be semi rigid or flexible. In the flexible walled IUD, the IUD may be inserted into the uterus in an uninflated condition and then subsequently expanded by filling with the solution containing the required concentration of the drug. The walls defining the cavity are permeable to the drug.

BRIEF DESCRIPTION OF THE DRAWINGS

The above and other embodiments of the present invention may be more fully understood from the following detailed description taken together with the accompanying drawing wherein similar reference characters refer to similar elements throughout and in which.

DESCRIPTION OF THE PREFERRED EMBODIMENTS

Figure 1:
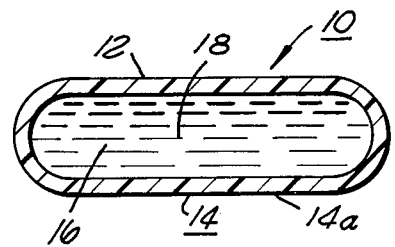
FIGS. 1 and 1A illustrate embodiments of an intrauterine device useful in the practice of the invention.

As noted above, the present invention is a medicated intra-uterine device wherein a preselected drug is provided in a concentrated solution in the cavity of the body member of an IUD. As utilized herein and in the appended claims, the term "drug" refers to one or a mixture of more than one of a preselected compound. The preselected compounds of the present invention are aromatic amidines and in particular the aromatic monoamidines, aromatic diamidines and non-aromatic diamidines. The aromatic amidines may be an aromatic monoamidine of the general formula:

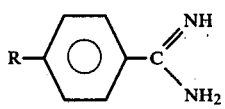

wherein: R is a carbon chain or an aromatic group with or without other elements, or, as preferred for utilization in the invention herein, an aromatic diamidine of the general formula:

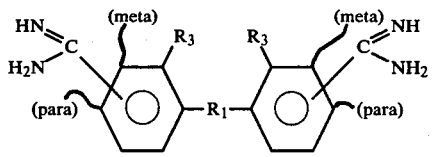

in which each amidine group

may be substituted in either a meta or para position with respect to $R_1$, and wherein:

$R_1$ is generally a carbon chain with or without ether bonds to the benzene rings;

$R_2$ and $R_3$ can be hydrogen, chlorine, bromine, iodine, hydroxyl group, alkyl, or other group; and

represents the benzene ring.

Table I below lists particular aromatic diamidines useful in the practice of the present invention.

TABLE I

| AROMATIC DIAMIDINES | | | | |
|---|---|---|---|---|
| Drug name | $R_1$ Carbon Chain | $R_2$ | $R_3$ | Relative Potency |
| Dibromopropamidine | $C_3H_6$ | Br | Br | 1.0 |
| Phenamidine | — | H | H | 0.2 |
| Octamidine | $C_8H_{16}$ | H | H | 2.6 |
| m-Pentamidine | $C_5H_{10}$ | H | H | 0.6 |
| Hexamidine | $C_6H_{12}$ | H | H | 1.6 |
| Dichlorohexamidine | $C_6H_{12}$ | Cl | Cl | 1.9 |
| Pentamidine | $C_5H_{10}$ | H | H | 2.4 |
| Monoiodohexamidine | $C_6H_{12}$ | I | H | 4.4 |

TABLE I-continued

| AROMATIC DIAMIDINES | | | | |
|---|---|---|---|---|
| Drug name | $R_1$ Carbon Chain | $R_2$ | $R_3$ | Relative Potency |
| Dibromopentamidine | $C_5H_{10}$ | Br | Br | 3.6 |
| Propamidine | $C_3H_6$ | H | H | 1.2 |
| Heptamidine | $C_7H_{14}$ | H | H | 1.9 |
| Diiodopentamidine | $C_5H_{10}$ | I | I | 6.8 |
| Diiodohexamidine | $C_6H_{12}$ | I | I | 7.5 |
| Butamidine | $C_4H_8$ | H | H | |
| Monochloropropamidine | $C_3H_6$ | Cl | H | |
| Monochlorobutamidine | $C_4H_8$ | Cl | H | |
| Monochloropentamidine | $C_5H_{10}$ | Cl | H | |
| Monochlorohexamidine | $C_6H_{12}$ | Cl | H | |
| Monochloroheptamidine | $C_7H_{14}$ | Cl | H | |
| Monochloroctamidine | $C_8H_{16}$ | Cl | H | |
| Monochlorononamidine | $C_9H_{18}$ | Cl | H | |
| Monobromopropamidine | $C_3H_6$ | Br | H | |
| Monobromofutamidine | $C_4H_8$ | Br | H | |
| Monobromopentamidine | $C_5H_{10}$ | Br | H | |
| Monobromohexamidine | $C_6H_{12}$ | Br | H | |
| Monobromoheptamidine | $C_7H_{14}$ | Br | H | |
| Monobromoctamidine | $C_8H_{16}$ | Br | H | |
| Monobromononamidine | $C_9H_{18}$ | Br | H | |
| Moniodopropamidine | $C_3H_6$ | I | H | |
| Monoidolobutamidine | $C_4H_6$ | I | H | |
| Monoiodopentamidine | $C_5H_{10}$ | I | H | |
| Monoiodohexamidine | $C_6H_{12}$ | I | H | |
| Monoiodoheptamidine | $C_7H_{14}$ | I | H | |
| Monoiodoctamidine | $C_8H_{16}$ | I | H | |
| Monoiodononamidine | $C_9H_{18}$ | I | H | |
| Dichloropropamidine | $C_3H_6$ | Cl | Cl | |
| Dichlorobutamidine | $C_4H_8$ | Cl | Cl | |
| Dichloropentamidine | $C_5H_{10}$ | Cl | Cl | |
| Dichlorohexamidine | $C_6H_{12}$ | Cl | Cl | |
| Dichloroheptamidine | $C_7H_{14}$ | Cl | Cl | |
| Dichloroctamidine | $C_5H_{16}$ | Cl | Cl | |
| Dichlorononamidine | $C_9H_{19}$ | Cl | Cl | |
| Dibromopropamidine (already listed) | $C_3H_6$ | Br | Br | |
| Dibromobutamidine | $C_4H_8$ | Br | Br | |
| Dibromopentamidine | $C_5H_{10}$ | Br | Br | |
| Dibromohexamidine | $C_6H_{12}$ | Br | Br | |
| Dibromoheptamidine | $C_7H_{14}$ | Br | Br | |
| Dibromoctamidine | $C_8H_{16}$ | Br | Br | |
| Dibromononamidine | $C_9H_{18}$ | Br | Br | |
| Diiodopropamidine | $C_3H_6$ | I | I | |
| Diiodobutamidine | $C_4H_8$ | I | I | |
| Diiodopentamidine | $C_5H_{10}$ | I | I | |
| Dioodohexamidine | $C_6H_{12}$ | I | I | |
| Diiodoheptamidine | $C_7H_{14}$ | I | I | |
| Diiodooctamidine | $C_8H_{16}$ | I | I | |
| Diiodononamidine | $C_9H_{18}$ | I | I | |
| Monochloromonobromopropamidine | $C_3H_6$ | Cl | Br | |
| Monochloromonobromobutamidine | $C_4H_8$ | Cl | Br | |
| Monochloromonobromopentamidine | $C_5H_{10}$ | Cl | Br | |
| Monochloromonobromohexamidine | $C_6H_{12}$ | Cl | Br | |
| Monochloromonobromoheptamidine | $C_7H_{14}$ | Cl | Br | |
| Monochloromonobromooctamidine | $C_8H_{16}$ | Cl | Br | |
| Monochloromonobromononamidine | $C_9H_{18}$ | Cl | Br | |
| Monochloromonoiodopropamidine | $C_3H_6$ | Cl | I | |
| Monochloromonoiodobutamidine | $C_4H_8$ | Cl | I | |
| Monochloromonoiodopentamidine | $C_5H_{10}$ | Cl | I | |
| Monochloromonoiodohexamidine | $C_6H_{12}$ | Cl | I | |
| Monochloromonoiidoheptamidine | $C_7H_{14}$ | Cl | I | |
| Monochloromonoiodooctamidine | $C_8H_{16}$ | Cl | I | |
| Monochloromonoiodononamidine | $C_9H_{18}$ | Cl | i | |

TABLE I-continued
AROMATIC DIAMIDINES

| DRUG | SPECIFIC FORMULA |
|---|---|
| 3,8-Di(m-amidinophenyldiazoamino)-5-ethyl-6-phenylphenanthridinium chloride dihydrochloride hydrate (aromatic diamidine) | (structure) |
| 8-(m-amidophenyldiazoamino)-3-amino-5-ethyl-6-phenylphenanthridinium chloride (aromatic monoamidine) | (structure) |
| 1,4-di (p-amidinophenoxy) cyclohexane (aromatic diamidine) | (structure) |
| 1,4-di (2-amidinovinyl) cyclohexane (nonaromatic diamidine) | (structure) |

| Drug name | $R_1$ Carbon Chain | $R_2$ | $R_3$ | Relative Potency |
|---|---|---|---|---|
| Monobromomonoiodo-propamidine | $C_3H_6$ | Br | I | |
| Monobromopronoiodo-butamidine | $C_4H_8$ | Br | I | |
| Monobromomonoiodo-pentamidine | $C_5H_{10}$ | Br | I | |
| Monobromonoiodo-hexamidine | $C_6H_{12}$ | Br | I | |
| Monobromomonoido-heptamidine | $C_7H_{14}$ | Br | I | |
| Monobromomonoiodo-octamidine | $C_8H_{16}$ | Br | I | |
| Monobromomonoiodo-nonamidine | $C_9H_{18}$ | Br | I | |

In addition to the specified aromatic diamidines listed in Table I, other aromatic diamidines, aromatic monomidines and non-aromatic dimiadines may also be utilized in accordance with the principles of the present invention.

Further, it has been found that the following compounds are also useful in the practice of the present invention:

The relative potency shown in Table 1 is expressed in relationship to dibromopropamidine, which has been discovered to be a highly potent fibrinolytic inhibitor. The numerical values are expressed as a reciprocal of the concentration of the drug producing the equivalent inhibition to the dibromopropamidine. Where no values for relative potency are listed such values have not been specifically determined.

Referring now to the drawing, there are illustrated in FIGS. 1 through 5 thereof various forms of IUDs useful in the practice of the present invention. According to the principles of the present invention many of the forms shown in FIGS. 1 through 5, as well as many other geometrical configurations of IUDs may be utilized in the practice of the present invention. Thus, the illustration of the IUDs illustrated in FIGS. 1 through 5 herein is not limiting to the principles of the practice of the present invention.

In the embodiment 10 of the intrauterine device shown in FIG. 1 it is generally comprised of a body member 12 having first walls 14 defining a fluid receiving cavity 16. In the embodiment 10 the first walls 14 are of a semi-flexible nature and are fabricated of, for example, the polymer of: 1. low density polyethylene or 2. Polyethyl vinyl acetate. In the embodiment 10, as can be seen, the cavity 16 is substantially coextensive with the first walls 14.

Contained within the cavity 16 is a concentrated fluid solution of the drug. The drug may be in a concentrated aqueous or organic or non-organic hydrophobic solution 18 within the cavity 16. The solution would be in a concentration range from 50 to 200 milligrams per milliliter or approximately 5 to 25% by weight. Additionally, the drug may also be provided in the form of a suspension.

Specifically, in the embodiment 10 shown in FIG. 1, wherein the wall 14 of the body member are semi-flexible, the drug could be provided in a crystalline form in the cavity 16 either with or without a solvent and in the range of 10 to 50% by weight. Further, instead of the crystalline form of the drug, the drug may consist of a concentrated paste with a minimal amount of solvent sufficient to provide the desired viscosity and/or consistency and providing the above-described concentration level. With the wall 14 of the body member 12 fabricated from the above-mentioned materials, the walls 14 are permeable to the drug contained within the cavity 16.

Figure 1A:
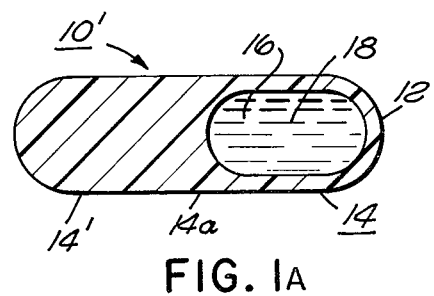

FIG. 1A illustrates another embodiment of the present invention generally designated 10' which is generally similar to the embodiment 10 of FIG. 1. However, in the embodiment 10', the cavity 16 is not coextensive with the first walls 14 but only extends in the region defined by the walls 14a. The walls 14' define the remainder of the body member 12 and no cavity is provided in this area. The concentrated fluid solution of the drug 18 is contained only within the cavity 16.

It will be appreciated, of course, that as utilized herein the term "concentrated fluid solution of the drug" also defines a concentrated fluid suspension of the drug.

Figure 2:
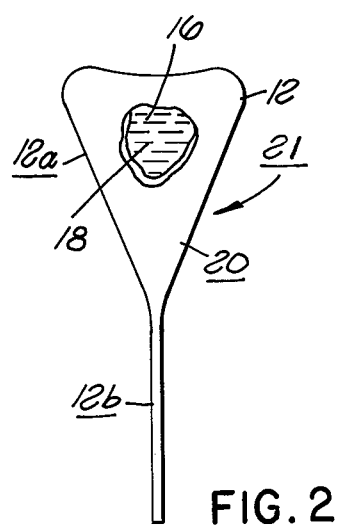
FIG. 2 illustrates another embodiment of an intrauterine device useful in the practice of the present invention.
Figure 3:
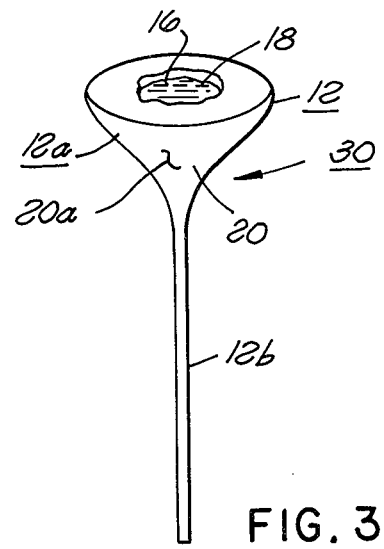
FIG. 3 illustrates another embodiment of an intrauterine device useful in the practice of the present invention.
Figure 4:
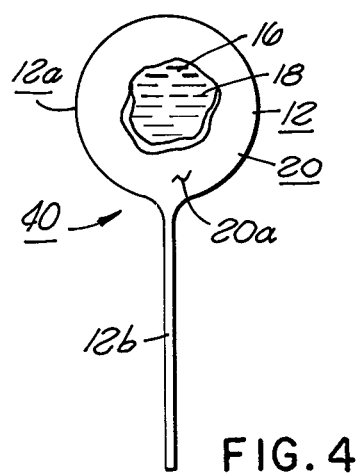
FIG. 4 illustrates another embodiment of an intrauterine device useful in the practice of the present invention.
Figure 5:
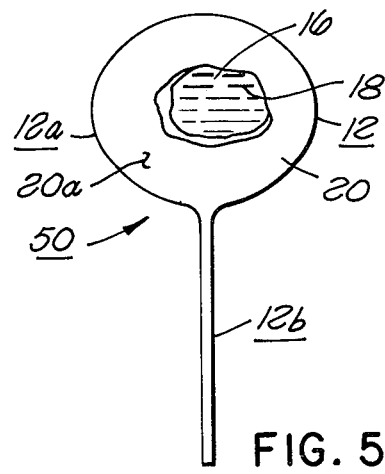
FIG. 5 illustrates another embodiment of an intrauterine device useful in the practice of the present invention.

In another embodiment of the present invention generally designated 21 as shown in FIG. 2, the IUD generally designated 12 having first walls 20 defining a cavity 16 in the upper portion 12a of the IUD 12. The first walls 20 are flexible walls and the upper portion 20a, in application, may be inserted into the uterus with the lower portion 12b of the body member 12 extending through the uterus, e.g., through the uterine cervical canal, the regions external to the uterus, e.g. the vagina. When inserted, the first walls 20 are collapsed so that it may be passed through the cervical canal into the uterine cavity. After insertion into the uterine cavity the cavity of the device 16 may be filled, thereby inflating the first wall 20 and cavity 16, and the device is thus filled with a concentrated solution of the drug generally designated 18. In this, and in the embodiments 30, 40 and 50 shown, respectively, in FIGS. 3, 4 and 5, the drug is provided in the form of the concentrated solution described above in connection with the embodiment 10 shown in FIG. 1. After the cavity 16 has been filled to the desired volume with the concentrated solution of the drug, the portion 12b of the body member 12 extending external to the uterus may be suitably sealed, for example, by tying a knot therein and the IUD left in place in the uterus for the desired time period. The embodiments 30, 40 and 50 shown in FIGS. 3, 4 and 5, respectively, are generally similar to the embodiment 21 shown in FIG. 2 except that the shape of the upper portion 12a of the body member 12 is provided in different shapes or configurations. That is, in embodiment 30 of FIG. 3 the upper portion 12a is in the form of a "top", in the embodiment 40 of FIG. 4 the upper portion 12a is in a spherical form. In the embodiment 50 of FIG. 5 the upper portion 12a is in an ovoid form. It will be appreciated that many other shapes may be provided for the upper portion 12a.

In the IUDs shown in FIGS. 1 through 5, the drug may, in addition to being provided in the cavity 16, also be provided in the walls 14 of FIG. 10 or walls 20 of FIGS. 2 through 5. Accordingly, the drug may be in a simple mixture with the polymer matrix defining the walls 14 or 20. The shape, charge, and other characteristics of the drug molecule such as its hydrophobicity, as well as similar characteristics of the polymer matrix of the walls 14 and 20 may be varied as desired to select the particular release rate of the drug from the walls of 14 and 20 to provide the desired total release rate of the drug into the intrauterine cavity when considering the release rate of the drug from the solution 18.

The ratio of the mixture of the drug contained within the walls 14 or 20 may be on the order of, for example, 10% to 50% by weight depending upon the potency of the drug and the particular polymer matrix from which the body member 12 is fabricated.

The drug may also be provided as a biodegradable polymer or copolymer and mixed into the walls 14 and 20 with selections of characteristics and ratios of weight as above defined.

The drug may also be provided in the biodegradable polymer or copolymer form and covalently bonded with the polymer matrix of the walls 14 or 20 of the body member 12 either within the walls or on the surface thereof.

Further, a biodegradable cross-linked polymer or copolymer coating of the drug bonded covalently to the outer surface 14a or 20a of the body member 12 to provide a soft hydrogel coating thereover. Such a coating is likely to be particularly effective in aiding retention of the IUD in the uterus during the time period soon after insertion thereof. The coating may be provided over all or part of the external surface 14a or 20a. The characteristics of the coating may be selected to provide the desired release rate of the drug into the uterine cavity when considered with the release of the drug from the solution 18 described above, or may be selected to provide specific additional release rates in certain portions thereof such as those in contact with the walls of the uterus.

Further, the drug may also be provided in a non-biodegradable monomer, dimer or olymer or a cross-linked polymer on the outer surface 14a or 20a of the body member 12. This coating may be provided by covalent or other chemical bonding between the drug molecules and the outer surface 14a or 20a. Since the bleeding of the endometrium is at the interface between the endometrium and the IUD, the solid phase and enzyme inhibition provided by the drug at the point of contact between the endometrium and the IUD can reduce the bleeding associated with utilization of an IUD.

Further, since, as noted above, copper release has also proven anti-conceptive in IUDs, a portion of the outer surface 14a or 20a may be provided with a coating of metallic copper such as a thin wire, copper plating, or the like.

It has been found that the drugs according to the present invention, and in particular the aromatic diamidines, while heretofore known to possess antiprotozoal, anti-bacterial, and anti-fungal effects, quite unexpectedly may also provide an anti-conceptive effect. It is believed that this effect, which should enhance the anti-conceptive effect of the intrauterine device itself, is due to the activity of the drug and its action on the very early embryo and possibly on the sperm.

Further, it is believed yet an additional unexpected and surprising result may be obtained due to the anti-proteolytic action of the drug. This effect is a reduction in the pain and/or cramps and expulsion heretofore associated with utilization of intrauterine devices including medicated IUDs.

The range of concentrations necessary to provide the desired effects mentioned above depend, of course, upon the particular drug or combinations selected. For example, for dipromopropamidine introduced into the uterine cavity and endometrial tissue water, and with an endometrial water turnover rate of 200 milliliters per day and with complete distribution of the drug in the endometrial water turned over, an intrauterine release rate of 50 to 200 mcg per day would be expected to produce a concentration of dipromopropamidine in the range of 0.5 to $2.0 \times 10^{-6}$ moles per liter in endometrial water. Since, in general, there will be less than complete distribution of the drug into the endometrial water turned over each day, the concentration of the drug in the uterine cavity could reach much higher levels; for example, on the order of $10^{-6}$ to $10^{-4}$ moles per liter. This concentration range is sufficient to provide both the anti-fibrinolytic effects, as well as the anti-conceptive or anti-fertility effects desired, and also, it is believed, the reduction in pain, cramps and expulsion. With the above release rate (50–200 mcg per day) and the known sizes of intrauterine devices currently available, and the amount of drug which can be incorporated into such devices, an effective life span of, for example, at least one to three years can be provided for such medicated devices.

Those skilled in the art, of course, can readily determine the appropriate release rate desired for any drug or combination thereof which may be utilized according to the principles of the present invention and, in accordance with known principles, establish the desired release rate thereof to achieve effectiveness.

Further, those skilled in the art may find many variations and adaptations of the present invention and all such variations and adaptations thereof falling within the scope and spirit of the invention are intended to be covered by the appended claims.

I claim:

1. In an intrauterine device of the type insertable in the uterus and having a surface contacting the uterus and first walls defining a fluid receiving cavity in at least a portion thereof, the improvement comprising, in combination:
   one of a concentrated fluid solution and suspension of a drug in said cavity and said drug of the type providing an antifibrinolytic, an antifertility and an antiproteolytic effect and said drug comprising an amidine; and
   said first walls of said intrauterine device comprising a polymer having a predetermined permeability to said drug,
   whereby, said predetermined permeability of said first walls controls the release rate of said drug from said cavity.

2. The arrangement defined in claim 1 wherein: said first walls are semi-flexible.

3. The arrangement defined in claim 1 wherein: said first walls define an inflatable cavity.

4. The arrangement defined in claim 1 wherein: said drug is selected from the class consisting of aromatic monoamidines, aromatic diamidines and non-aromatic diamidines.

5. The arrangement defined in claim 1 and further comprising:
   a coating on at least a portion of said surface of said intrauterine device, and said coating comprising one of a biodegradable cross-linked polymer and co-polymer of a drug selected from the same group as said drug in said cavity.

6. The arrangement defined in claim 1 and further comprising:
   a coating on at least some of said surfaces of said intrauterine device, and said coating comprising one of a non-biodegradable monomer, dimer, oligomer and cross-linked polymer of a drug selected from the same group as said drug in said cavity.

7. The arrangement defined in claim 2 wherein: said drug is selected from the class consisting of aromatic monoamidines, aromatic diamidines and non-aromatic diamidines.

8. The arrangement defined in claim 2 and further comprising:
   a coating on at least a portion of said surface of said intrauterine device, and said coating comprising one of a biodegradable cross-linked polymer and co-polymer of a drug selected from the same group as said drug in said cavity.

9. The arrangement defined in claim 2 and further comprising:
   a coating on at least some of said surfaces of said intrauterine device, and said coating comprising one of a non-biodegradable monomer, dimer, oligomer and cross-linked polymer of a drug selected from the same group as said drug in said cavity.

10. The arrangement defined in claim 3 wherein: said drug is selected from the class consisting of aromatic diamidines of the group

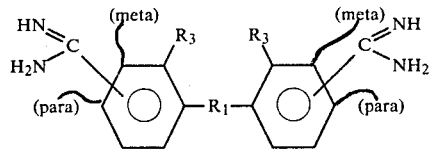

in which each amidine group

may be substituted in either a meta or para position with respect to $R_1$ $R_1$ is selected from the group consisting of $C_xH_y$; and $R_2$ and $R_3$ are selected from the group consisting of hydrogen, chlorine, bromine, iodine, hydroxyl group and alkyl groups; and

represents the benzene ring.

11. The arrangement defined in claim 3 wherein:
said drug is selected from the class consisting of:
- 3,8-Di (m-amidinophenyldiazoamino)-5-ethyl-6-phenylphenanthridinium chloride dihydrochloride hydrate
- 8-m(m-Amiophenyldiazoamino)-3-amino-5-ethyl-6-phenylphenanthridinium chloride,
- 1,4-di (p-amidinophenoxy) cyclohexane, and
- 1,4-di (2 amidinovinyl) cyclohexane.

12. The arrangement defined in claim 3 wherein:
said drug also provides a reversible anti-conceptive effect.

13. The arrangement defined in claim 3 and further comprising:
a coating on at least a portion of said surface of said intrauterine device, and said coating comprising one of a biodegradable cross-linked polymer and co-polymer of a drug selected from the same group as said drug in said cavity.

14. The arrangement defined in claim 3 and further comprising:
a coating on at least some of said surfaces of said intrauterine device, and said coating comprising one of a non-biodegradable monomer, dimer, oligomer and cross-linked polymer of a drug selected from the same group as said drug in said cavity.

15. The arrangement defined in claim 7 wherein:
said drug is selected from the class consisting of aromatic diamidines of the group

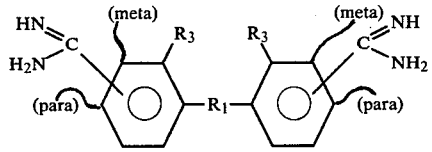

in which each amidine group

may be substituted in either a meta or para position with respect to $R_1$ $R_1$ is selected from the group consisting of $C_xH_y$; and $R_2$ and $R_3$ are selected from the group consisting of hydrogen, chlorine, bromine, iodine, hydroxyl group and alkyl groups; and

represents the benzene ring.

16. The arrangement defined in claim 7 wherein:
said drug is selected from the class consisting of:
- 3,8-Di (m-amidinophenyldiazoamino)-5-ethyl-6-phenylphenanthridinium chloride dihydrochloride hydrate
- 8-m(m-Aminophenyldiazoamino)-3-amino-5-ethyl-6-phenylphenanthridinium chloride,
- 1,4-di (p-amidinophenoxy) cyclohexane, and
- 1,4-di (2 amidinovinyl) cyclohexane.

17. The arrangement defined in claim 13 wherein:
said drug is selected from the class consisting of aromatic diamidines of the group

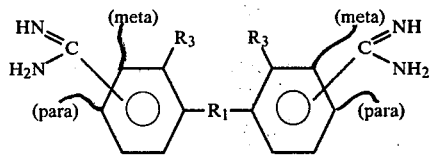

in which each amidine group

may be substituted in either a meta or para position with respect to $R_1$ $R_1$ is selected from the group consisting of $C_xH_y$; and $R_2$ and $R_3$ are selected from the group consisting of hydrogen, chlorine, bromine, iodine, hydroxyl group and alkyl groups; and

represents the benzene ring.

18. The arrangement defined in claim 13 wherein:
said drug is selected from the class consisting of:
- 3,8-Di (m-amidinophenyldiazoamino)-5-ethyl-6-phenylphenanthridinium chloride dihydrochloride hydrate
- 8-m(m-Amiophenyldiazoamino)-3-amino-5-ethyl-6-phenylphenanthridinium chloride,
- 1,4-di (p-amidinophenoxy) cyclohexane, and
- 1,4-di (2 amidinovinyl) cyclohexane.

19. The arrangement defined in claim 13 wherein:
said drug is selected from the class consisting of aromatic monoamidines, aromatic diamidines and non-aromatic diamidines.

20. The arrangement defined in claim 13 wherein:
said drug also provides a reversible anti-conceptive effect.

21. The arrangement defined in claim 13 further comprising:
a coating of copper on a portion of the surface of said body member.

22. The arrangement defined in claim 14 wherein:
said drug is selected from the class consisting of aromatic diamidines of the group

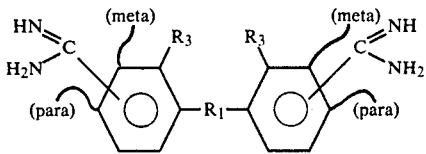

in which each amidine group

may be substituted in either a meta or para position with respect to $R_1$ $R_1$ is selected from the group consisting of $C_xH_y$; and $R_2$ and $R_3$ are selected from the group consisting of hydrogen, chlorine, bromine, iodine, hydroxyl group and alkyl groups; and

represents the benzene ring.

23. The arrangement defined in claim 14 wherein: said drug is selected from the class consisting of:
3,8-Di (m-amidinophenyldiazoamino)-5-ethyl-6-phenylphenanthridinium chloride dihydrochloride hydrate
8-m(m-Amiophenyldiazoamino)-3-amino-5-ethyl-6-phenylphenanthridinium chloride,
1,4-di (p-amidinophenoxy) cyclohexane, and
1,4-di (2 amidinovinyl) cyclohexane.

24. The arrangement defined in claim 14 wherein: said drug is selected from the class consisting of aromatic monoamidines, aromatic diamidines and non-aromatic diamidines.

25. The arrangement defined in claim 14 wherein: said drug also provides a reversible anticonceptive effect.

26. The arrangement defined in claim 16 further comprising:
a coating of copper on a portion of the surface of said body member.

27. In an intrauterine device of the type insertable in the uterus and having a surface contacting the uterus and first walls defining a fluid receiving cavity in at least a portion thereof, the improvement comprising, in combination:
a drug in said cavity and said drug of the type providing an antifibrinolytic, an antifertility and an antiproteolytic effect and said drug comprising an amidine; and
said walls of said intrauterine device comprising a polymer having a predetermined permeability to said drug,
whereby, said predetermined permeability of said first walls controls the release rate of said drug from said cavity.

28. The arrangement defined in claim 27 wherein: said first walls are semi-flexible.

29. The arrangement defined in claim 28 wherein: said drug is in a crystalline form.

30. The arrangement defined in claim 28 wherein: said drug is in the form of a paste.

31. The arrangement defined in claim 28 further comprising:
a coating of copper on a portion of the surface of said body member.

32. The arrangement defined in claim 28 wherein said drug is selected from the group consisting of aromatic monoamidines, aromatic diamidines and non-aromatic diamidines.

* * * * *